United States Patent [19]

Sunday et al.

[11] Patent Number: 4,571,402

[45] Date of Patent: * Feb. 18, 1986

[54] ANTI-BRONCHOCONSTRICTION 2-(4'-PYRIDINYL)-THIAZOLE DERIVATIVES, COMPOSITION, AND METHOD OF USE THEREFOR

[75] Inventors: Brooks R. Sunday, Oakland; Joseph T. Witkowski, Morris Township, Morris County, both of N.J.

[73] Assignee: Schering Corporation, Kenilworth, N.J.

[*] Notice: The portion of the term of this patent subsequent to Jul. 9, 2002 has been disclaimed.

[21] Appl. No.: 492,848

[22] Filed: May 9, 1983

Related U.S. Application Data

[63] Continuation-in-part of Ser. No. 391,061, Jun. 22, 1982.

[51] Int. Cl.[4] .................... A01N 43/40; A61K 31/44; C07D 417/04
[52] U.S. Cl. ................... 514/336; 546/280; 546/278
[58] Field of Search ............... 546/280, 278; 424/263; 514/336

[56] References Cited

U.S. PATENT DOCUMENTS

| | | | |
|---|---|---|---|
| 3,551,436 | 12/1970 | Bauer et al. | 546/280 |
| 3,551,437 | 12/1970 | Bauer et al. | 546/280 |
| 3,555,036 | 1/1971 | Bauer et al. | 546/280 |
| 3,703,577 | 4/1972 | Bauer et al. | 546/280 |
| 3,821,384 | 6/1974 | Ariyan et al. | 424/263 |
| 3,842,172 | 10/1974 | Ariyan et al. | 424/263 |
| 3,852,293 | 12/1974 | Ariyan et al. | 546/280 |
| 3,980,659 | 9/1976 | Fleckenstein et al. | 424/263 |
| 4,260,609 | 4/1981 | Baldwin et al. | 546/280 |
| 4,528,291 | 7/1985 | Witkowski et al. | 546/280 |

FOREIGN PATENT DOCUMENTS

| | | | |
|---|---|---|---|
| 1598975 | 8/1970 | France | 546/280 |
| 1382854 | 2/1975 | United Kingdom | 424/263 |

OTHER PUBLICATIONS

Chemical Abstracts, vol. 49, 6952, 1954, Jan Bartz et al.
Journal of Organic Chemistry, vol. 22, No. 8, Aug. 1957, pp. 984–986, Washington, DC, US; T. S. Gardner et al., "Synthesis of compounds for Chemotherapy of Tuberculosis, VII, Pyridine N-Oxides with Sulfur-Containing Groups".
Journal of Medicinal Chemistry, vol. 23, No. 1, Jan. 1980, pp. 65–70, Washington, DC, US; J. J. Baldwin et al.: "Heterocyclic Analogues of the Antihypertensive Beta-Adrenergic Blocking Agent (S)-2-[3-tert-butylamino)-2-hydroxypropoxy]-3-cyanopyridine".
Justus Liebigs Annalen Der Chemie, vol. 717, Nov. 1968, Verlag Chemie, pp. 148–153, Washington, DC, US; A. Benko et al.: "Neue Rimifon-Analoga mit Thiazol-Ring".
Journal of Medicinal Chemistry, vol. 12, No. 9, Sep. 1969, pp. 891–893, Washington, DC, US: D. A. Blickens et al.: "Quaternary Thiazolylpyridinium Salts, Oral Hypoglycemic Agents".

*Primary Examiner*—Henry R. Jiles
*Assistant Examiner*—J. G. Mullins
*Attorney, Agent, or Firm*—James R. Nelson; Stephen I. Miller

[57] ABSTRACT

Certain 2-(4'-pyridinyl)-thiazoles additionally substituted in either the 4- or 5- position are bronchodilating agents. Methods for their preparation and use are disclosed.

6 Claims, No Drawings

ANTI-BRONCHOCONSTRICTION 2-(4'-PYRIDINYL)-THIAZOLE DERIVATIVES, COMPOSITION, AND METHOD OF USE THEREFOR

CROSS REFERENCE TO RELATED APPLICATION

This application is a continuation in part of copending application Ser. No. 391,061, filed June 22, 1982.

BACKGROUND OF THE INVENTION

Variously substituted 2-(4'-pyridinyl)-thiazole derivatives are described as potential tuberculostatic agents in Liebigs Ann. Chem., 717, 148 (1968) [C.A. 70, 37693Z (1969)].

Various 2-(3'-pyridinyl)-thiazoles are described in U.S. Pat. Nos. 3,821,384; 3,842,172; 3,852,293, and in U.K. Pat. No. 1,382,854.

The Journal of Organic Chemistry, 22, 984 (1957) describes 5-methyl-2-(4-pyridinyl)-4(5H)-thiazolone and 4-methyl-2-(4'-pyridinyl)-thiazole.

The present invention discloses 2-(4'-pyridinyl)-thiazoles which are additionally substituted in either the 4- or 5- position. These compounds are useful as bronchodilator agents.

SUMMARY OF THE INVENTION

The invention sought to be patented in its chemical compound aspect is a compound having the structural formula I

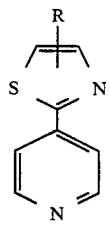

wherein R is cyano,

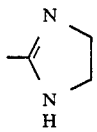

or —C(=X)NHY; wherein X is O, S or NH and Y is hydrogen, hydroxy, alkyl having from 1 to 6 carbon atoms or hydroxyalkyl having from 1 to 6 carbon atoms, and the pharmaceutically acceptable salts thereof; provided that N-methyl-2-(4'-pyridinyl)-thiazole4-carboxamide is excluded.

The invention sought to be patented in its pharmaceutical composition aspect is a composition useful for treating bronchoconstriction in a mammal which comprises a compound having structural formula I in a combination with a pharmaceutically acceptable carrier.

The invention sought to be patented in its pharmaceutical method aspect is a method for treating bronchoconstriction in a mammal which comprises administering the above-defined pharmaceutical composition to said mammal.

DESCRIPTION OF THE INVENTION

The compounds of the invention may be prepared from thioisonicotinamide, II by known methods.

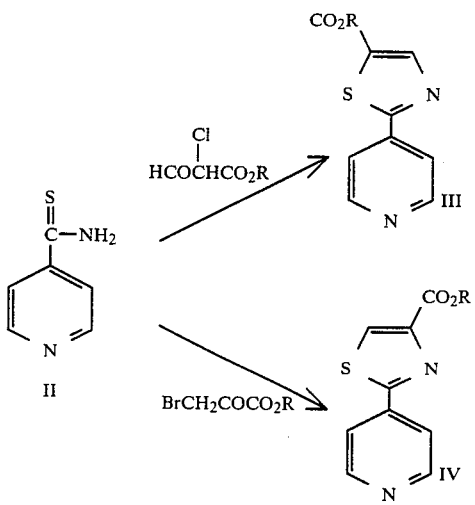

Thus, condensation of II with either methyl 2-chloroformylacetate or ethyl bromopyruvate, for example, yields respectively methyl 2-(4'-pyridinyl)-thiazole-5-carboxylate III, or ethyl 2-(4'-pyridinyl)-thiazole-4-carboxylate IV. The carboxyl functions of compounds III and IV may be readily converted to the corresponding nitrile, an amide, a thioamide, an amidine or the 2-imidazoline if desired by methods known to those skilled in the art.

When utilized herein the term "alkyl" means such groups having straight or branched chains and having from 1 to 6 carbon atoms; the term "hydroxyalkyl" means an alkyl group as herein defined which is substituted with a hydroxyl group.

Certain compounds of the invention may exist in isomeric forms. The invention contemplates all such isomers both in pure form and in mixture, including racemic mixtures.

The compounds used in the methods of this invention can be used to treat allergy caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The bronchodilating effect of the compounds of this invention is identified by tests which measure a compound's inhibition of anaphylatic bronchospasm in sensitized guinea pigs having antigen induced bronchoconstriction. For example, the compound 2-(4'-pyridinyl)-thiazole-4-thiocarboxamide was found to inhibit anaphylatic bronchospasms in such test procedure when given at an intravenous dose of 10 mg/kg. The compounds are effective non-adrenergic, antianaphylactic agents. When administered parenterally, e.g., intravenously, the compounds are active at dosages from about 0.1–10 mg/kg body weight.

The compounds of the invention of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

The compounds of the invention form salts with pharmaceutically acceptable acids such as hydrochloric, sulfuric, hydrobromic, phosphoric, acetic, fumaric, benzoic and the like.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use. Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

PREPARATIVE EXAMPLES

PREPARATIVE EXAMPLE A

Methyl 2-(4'-Pyridinyl)-thiazole-5 carboxylate

Add 18.0 gm of methyl 2-chloroformylacetate to 18.2 gm of thioisonicotinamide in 250 ml of methanol. Heat the system to reflux for 22 hours. Stop the reaction and cool the system in an ice bath. Filter to yield methyl 2-(4'-pyridinyl)-thiazole-5-carboxylate, m.p. 163°–165° C.

PREPARATIVE EXAMPLE B

Ethyl 2-(4'-Pyridinyl)-thiazole-4-carboxylate hydrobromide 1/4 hydrate

Add 70.0 gm of ethyl bromopyruvate to 41.5 gm of thioisonicotinamide in 600 ml of absolute ethanol. Heat the system at reflux for 2 ½ hours. Stop the reaction and cool the system to room temperature. Filter the solid from solution and recrystallize the solid from absolute ethanol to give the ethyl 2-(4'-pyridinyl)-thiazole-4-carboxylate hydrobromide ¼ hydrate, m.p. 217°–222° C.

EXAMPLES

Example I 2-(4'-Pyridinyl)-thiazole-4-carboxamide

Add 25.0 gm of ethyl 2-(4'-pyridinyl)-thiazole-4-carboxylate hydrobromide ¼ hydrate to 300 ml of 20% ammonia in methanol in a steel bomb cooled to 0° to 5°

C. Heat the system in an oil bath at 65° C. for 48 hours. Stop the reaction and cool the system to room temperature. Remove the solvent by stripping to yield a solid residue. Crystallize the residue from aqueous ethanol to give the 2-(4'-pyridinyl)-thiazole-4-carboxamide, m.p. 201°-204.5° C.

Example II 2-(4'-Pyridinyl)-thiazole-5-carboxamide

Add 10.0 gm of methyl 2-(4'-pyridinyl)-thiazole-5-carboxylate to 200 ml of 20% ammonia in methanol in a steel bomb cooled to 0° C. to 5° C. Heat the system in an oil bath to 80° C. for 70 hours. Stop the reaction and cool the system to room temperature. Remove the solvent by stripping to yield a solid residue. Crystallize the residue from aqueous ethanol to give 2-(4'-pyridinyl)-thiazole-5-carboxamide, m.p. 267°-270° C.

Example III

N-(2-Hydroxyethyl)-2-(4'-pyridinyl)-thiazole-4-carboxamide ¼ hydrate

Add 3.5 gm of ethyl 2-(4'-pyridinyl)-thiazole-4-carboxylate hydrobromide ¼ hydrate to a steel bomb containing 5 ml of ethanolamine in 75 ml of ethanol. Heat the system in al oil bath at 100° C. for 20 hours. Cool the system to room temperature and remove the solvent by stripping. Partition the residue between chloroform and water. Dry the chloroform solution over anhydrous magnesium sulfate, filter and remove the solvent by stripping. Crystallize the residue from aqueous ethanol to give N-(2-hydroxyethyl)-2-(4'-pyridinyl)-thiazole-4-carboxamide ¼ hydrate, m.p. 159°-162° C.

Similarly prepared by following the above procedure with the appropriate reagents are:
A. N-Ethyl-2-(4'-pyridinyl)-thiazole-5-carboxamide
B. N-(2-Hydroxyethyl)-2-(4'-pyridinyl)-thiazole-5-carboxamide

Example IV

4-Cyano-2-(4'-pyridinyl)-thiazole

Add 10.8 gm of p-toluenesulfonyl chloride to 5.20 gm of 2-(4'-pyridinyl)-thiazole-4-carboxamide in 100 ml of pyridine cooled to 0° to 5° C. Heat the system to 90° C. in an oil bath for 18 hours. Remove the solvent by stripping and dissolve the residue in 200 ml of 1N hydrochloric acid. Extract the acid solution with chloroform. Cool the aqueous solution to 0° to 5° C. and then add 1N sodium hydroxide solution until the system is alkaline. Extract the product from this solution with chloroform. Wash the chloroform solution with water and then dry the chloroform solution with anhydrous magnesium sulfate. Filter the solution and remove the solvent by stripping to give the 4-cyano-2(4'-pyridinyl)-thiazole, m.p. 181.5°-182.5° C.

By following the above procedure and utilizing 2-(4'-pyridinyl)-thiazole-5-carboxamide as starting material, one will obtain 5-cyano-2-(4'-pyridinyl)-thiazole.

Example V 2-(4'-Pyridinyl)-thiazole-4-thiocarboxamide

Dissolve 2.0 gm of 4-cyano-2-(4'-pyridinyl)thiazole in 25.0 gm of pyridine. Add 1.5 ml of triethylamine to the system. Cool the system to 0° to 6° C. and treat the system with hydrogen sulfide gas until the reaction is complete as indicated by thin layer chromatography. Pour the reaction mixture into icewater and filter to give 2-(4'-pyridinyl)-thiazole-4-thiocarboxamide, m.p. 178°-180° C.

By following the above procedure and using 5-cyano-2-(4'-pyridinyl)-thiazole as starting material, one will obtain 2-(4'-pyridinyl)-thiazole-5-thiocarboxamide.

Example VI 2-(4'-Pyridinyl)-thiazole-4-carboxamidine hydrochloride

Add 0.30 gm of sodium methoxide to 3.73 gm of 4-cyano-2-(4'-pyridinyl)-thiazole in 400 ml of methanol and stir under nitrogen at room temperature for 16 hours. Add 1.08 gm of ammonium chloride and heat at reflux for 4 hours. Remove one-half the solvent by distillation. Cool in an ice bath and filter to give 2-(4'-pyridinyl)-thiazole-4-carboxamidine hydrochloride, m.p. 340° C. (dec).

Similarly prepared by following the above procedure with the appropriate reagents are:
A. 2-(4'-Pyridinyl)-thiazole-4-(N-normal butyl)-carboxamidine hydrochloride hemihydrate, m.p. 162° C.
B. 2-(4'-Pyridinyl)-thiazole-4-(N-ethyl)-carboxamidine hydrochloride 0.3/4 hydrate, m.p. 264°-267° (dec)
C. 2-(4'-Pyridinyl)-thiazole-4-(N-methyl)-carboxamidine hydrochloride, m.p. 345°-348° C. (dec).
D 2-(4'-Pyridinyl)-thiazole-5-carboxamidine hydrochloride.

Example VII 2-(4'-Pyridinyl)-4-(2-imidazolin-2-yl)-thiazole

Add 0.18 gm of sodium methoxide to 1.75 gm of 4-cyano-2-(4'-pyridinyl)-thiazole in 300 ml of methanol and stir overnight under nitrogen at room temperature. Remove the solvent by stripping. Partition the residue between cold water and cold chloroform. Dry the chloroform solution over anhydrous sodium sulfate, filter and remove the solvent by stripping at room temperature. Add 50 ml of absolute ethanol and 1.56 ml of ethylenediamine and heat at 60° to 70° C. for 52 hours. Remove the solvent by stripping and partition the residue between water and chloroform. Wash the chloroform solution with water and dry over anhydrous magnesium sulfate. Filter and remove the solvent by stripping to give a solid residue. Recrystallize the product from benzene to give 2-(4'-pyridinyl)-4-(2-imidazolin-2-yl)-0 thiazole, m.p. 139-141° C.

A. By following the above procedure and using 5-cyano-2-(4'-pyridinyl)-thiazole as starting material, one will obtain 2-(4'-pyridinyl)-5-(2-imidazolin-2-yl)-thiazole.

Example VIII 2-(4'-Pyridinyl)-thiazole-4-carboxamidoxime hydrochloride

Add a solution of 0.56 gm of hydroxylamine hydrochloride in 25 ml of water to a solution of 1.50 gm of 4-cyano-2-(4'-pyridinyl)-thiazole in 300 ml of warm ethanol. Heat at reflux until the reaction is complete as indicated by thin-layer chromatography on silica gel eluted with ethyl acetate. Cool the reaction mixture in an ice bath and filter the resulting suspension to give 2-(4'-pyridinyl)-thiazole-4-carboxamidoxime hydrochloride, m.p. 258°-260° C. (dec).

A. By following the above procedure and utilizing 5-cyano-2-(4'-pyridinyl)-thiazole as starting material, one will obtain 2-(4'-pyridinyl)-thiazole-5-carboxamidoxime hydrochloride.

We claim:

1. A compound having the structural formula I

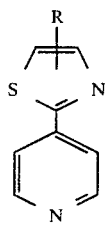

wherein
R is cyano,

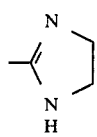

—C(=X)NHY wherein X is O, S or NH; and
Y is hydrogen, hydroxy, alkyl having from 1 to 6 carbon atoms, or hydroxyalkyl having from 1 to 6 carbon atoms, and the pharmaceutically acceptable salts thereof; provided that N-methyl-2-(4'-pyridinyl)-thiazole-4-carboxamide ,2-(4'-pyridinyl)-thiazole-4-carboxamide, and 4-cyano-2-(4'-pyridinyl)-thiazole are excluded.

2. The compounds defined in claim 1 having the structural formula

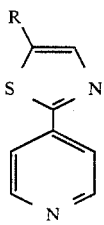

and the pharmaceutically acceptable salts thereof.

3. The compounds defined in claim 1 having the structural formula

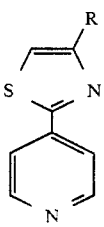

and the pharmaceutically acceptable salts thereof.

4. The compounds defined in claim 1 having the names:
2-(4'-pyridinyl)-thiazole-4-thiocarboxamide;
2-(4'-pyridinyl)-thiazole-5-carboxamide;
N-(2-hydroxyethyl)-2-(4'-pyridinyl)-thiazole-4-carboxamide;
2-(4'-pyridinyl)-thiazole-4-carboxamidoxime;
2-(4'-pyridinyl)-thiazole-4-carboxamidine;
2-(4'-pyridinyl)-4-(2-imidazolin-2-yl)-thiazole; and
the pharmaceutically acceptable salts thereof.

5. A pharmaceutical composition useful for treating bronchoconstriction in a mammal which comprises an antibronchoconstrictionally effective amount of a compound having structural formula I

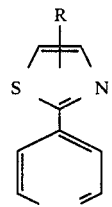

wherein
R is cyano,

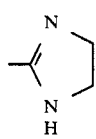

or —C(=X)NHY wherein X is 0, S or NH; and
Y is hydrogen, hydroxy, alkyl having from 1 to 6 carbon atoms, or hydroxyalkyl having from 1 to 6 carbon atoms, and the pharmaceutically acceptable salts thereof; provided that N-methyl-2-(4'-Pyridinyl)-thiazole-4-carboxamide, 2-(4'-pyridinyl)-thiazole-4-carboxamide, and 4-cyano-2-(4'-pyridinyl)-thiazole are excluded,
in combination with a pharmaceutically acceptable carrier.

6. A method for treating bronchoconstriction in a mammal which comprises administering an antibronchoconstrictionally effective amount of a compound having structural formula I

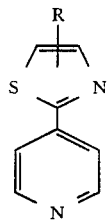

in combination with a pharmaceutically acceptable carrier, wherein
R is cyano,

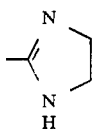

or —C(=X)NHY wherein X is O, S or NH; and
Y is hydrogen, hydroxy, alkyl having from 1 to 6 carbon atoms, or hydroxyalkyl having from 1 to 6 carbon atoms, and the pharmaceutically acceptable salts thereof; provided that N-methyl-2(4'-pyridinyl)-thiazole-4-carboxamide is excluded.

* * * * *